United States Patent
Mochizuki et al.

(10) Patent No.: US 7,375,364 B2
(45) Date of Patent: May 20, 2008

(54) RECORDING SHEET USAGE COUNT EVALUATION METHOD AND APPARATUS, AND MEDICAL IMAGE PROCESSING APPARATUS

(75) Inventors: Naoki Mochizuki, Kaisei-machi (JP); Yasunori Ohta, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/389,085

(22) Filed: Mar. 27, 2006

(65) Prior Publication Data

US 2006/0219964 A1    Oct. 5, 2006

(30) Foreign Application Priority Data

Apr. 1, 2005   (JP)   ............................. 2005-106415

(51) Int. Cl.
*B65H 5/00* (2006.01)

(52) U.S. Cl. .................. 250/589; 250/584; 235/375; 235/377

(58) Field of Classification Search ............... 250/589, 250/584; 235/375, 377

See application file for complete search history.

(56) References Cited

U.S. PATENT DOCUMENTS

| | | | | |
|---|---|---|---|---|
| 4,739,480 A | * | 4/1988 | Oono et al. .................. | 250/584 |
| 4,789,782 A | * | 12/1988 | Ohara ......................... | 250/583 |
| 4,893,011 A | * | 1/1990 | Bauer et al. ................. | 250/589 |
| 6,811,079 B1 | * | 11/2004 | Vraa et al. ................... | 235/383 |

FOREIGN PATENT DOCUMENTS

| | | |
|---|---|---|
| JP | 2001-154297 A | 6/2001 |
| JP | 2003-220054 A | 8/2003 |

* cited by examiner

*Primary Examiner*—David Porta
*Assistant Examiner*—Jessica L Eley
(74) *Attorney, Agent, or Firm*—Sughrue Mion, PLLC (57) ABSTRACT

A recording sheet usage count evaluation method enabling, even when plural radiation imaging apparatuses and plural radiographic image reading apparatuses exist, accurate evaluation of cumulative working frequencies of recording sheets commonly used in those apparatuses. The method includes the steps of (a) receiving recording sheet identification information with image data from a radiographic image reading apparatus; (b) counting a usage count of each recording sheet on a basis of the recording sheet identification information received at step (a), weighting a count value in accordance with a set condition, and accumulating the weighted count value to store the accumulated count value in correspondence with the recording sheet identification information; and (c) calculating a total count value for each recording sheet by referring to count values stored in other medical image processing apparatuses and adding the count values to the count value stored at step (b).

15 Claims, 8 Drawing Sheets

RECORDING SHEET USAGE COUNT EVALUATION METHOD AND APPARATUS, AND MEDICAL IMAGE PROCESSING APPARATUS

BACKGROUND OF THE INVENTION

1. Field of the Invention

The present invention relates to recording sheet usage count evaluation method and apparatus for evaluating a cumulative usage count of each recording sheet (also called "imaging plate") in a radiation imaging system, in which a radiographic image is recorded on the recording sheet by imaging an object by using a radiation imaging apparatus, image data is obtained by reading the radiographic image recorded on the recording sheet by using a radiographic image reading apparatus, and the image data is processed by using a medical image processing apparatus. Further, the present invention relates to a medical image processing apparatus using such a recording sheet usage count evaluation method.

2. Description of a Related Art

Conventionally, an imaging method using a radiation (X-ray, α-ray, β-ray, γ-ray, electron beam, ultraviolet ray, or the like) is utilized in various fields, and particularly, employed as one of the most important means for diagnosis in a medical field. Since a first X-ray photograph was realized, X-ray photography has been repeatedly improved, and presently, a method using a combination of a fluorescent screen and an X-ray film is going mainstream. On the other hand, in recent years, various digitized apparatuses such as X-ray CT apparatus, ultrasonic apparatus or MRI apparatus are in practical use, and construction of diagnosis information processing systems in hospitals is being developed. As for X-ray images also, many studies have been made for digitization, and a radiation imaging method using a photostimulable phosphor has been established, which attracts many attentions as a method that will replace conventional X-ray photography.

The photostimulable phosphor (storage phosphor) is a substance in which a portion of radiation energy is stored when the radiation is irradiated thereon, and thereafter, stimulated fluorescence is emitted according to the stored energy when excitation light such as visible light is irradiated thereon. The existence of the photostimulable phosphor has conventionally been known. The radiation imaging method using the photostimulable phosphor will be described below. First, by using a radiation imaging apparatus, a radiographic image of an object such as a human body is taken on a recording sheet (imaging plate), onto which photostimulable phosphor is applied, and recorded thereon. Then, by using a radiographic image reading apparatus, the recording sheet is scanned with excitation light such as a laser beam, and thereby, stimulated fluorescent light is read out photoelectrically to obtain image data. Further, by using a medical image processing apparatus, after the image data is properly processed, the radiographic image is output on a display such as a CRT, or printed out on a film by using a laser printer, etc., and thus, the radiographic image can be displayed as a visual image.

Such a radiation imaging method has a performance comparable to the conventional X-ray photography in terms of imaging sensitivity and image quality. For example, as compared to the conventional X-ray photography, the exposure range is extremely large, and the response of the stimulated fluorescent light to the light exposure is substantially proportional throughout the whole exposure range. Accordingly, when the object is imaged under any radiation dose, it is possible to capture the luminescent range of the image existent therein, and obtain a digitized signal through normalization without shortage or excess. Also, by combining the obtained signal with a proper image processing method, it is possible to constantly provide an image of excellent quality under a variety of imaging conditions. Further, because of direct acquisition of digitized image information, not only long-term preservation of a large amount of data without deterioration, but also development for use in a medical diagnosis information system becomes possible.

Now, generally, the recording sheet is contained into a case, called "cassette", when in use. As an identification mark for distinguishing a recording sheet for imaging one patient from a recording sheet for imaging another patient, a barcode is attached to the recording sheet, which can be viewed through a window provided on the cassette.

When the recording sheet contained in the cassette is repeatedly used for radiation imaging and radiographic image reading, the characteristic thereof is degraded because of bending in the radiographic image reading apparatus or secular change, which tends to bring about deterioration of the image quality. In order to estimate such image quality deterioration beforehand, it is desired to confirm a cumulative usage count of each recording sheet.

However, in general, the recording sheet is neither specified for each radiation imaging apparatus nor specified for each radiographic image reading apparatus, but commonly used for a plurality of radiation imaging apparatuses or a plurality of radiographic image reading apparatuses. Therefore, it has not been realized to confirm the cumulative usage count of each recording sheet. Further, the degree of degradation in the characteristic of the recording sheet varies with difference in type of the radiographic image reading apparatuses, difference in installation environment of the radiographic image reading apparatuses and difference in manufactured time of the recording sheets, and therefore, it is desired to confirm the usage state of the recording sheet, taking into account at least one of the above factors.

As a related art, Japanese Patent Application Publication JP-P2001-154297A discloses, in an image information record reading apparatus of a built-in type, to efficiently perform confirmation of the necessity for cleaning and exchange of sheets. In the image information record reading apparatus, there are provided counter means for counting the frequency of feeding a sheet (IP: imaging plate), a display panel for indicating a counted count value, and a buzzer for generating a warning beep depending on a predetermined frequency when the count value reaches the predetermined frequency. By using the count value indicated on the display panel or the warning beep generated by the buzzer, a user can decide the necessity of cleaning or exchange of the sheet (IP).

However, the art disclosed in the above JP-P2001-154297A is limited to an image information record reading apparatus of a build-in type, and it is not possible to apply to a general system in which a recording sheet is commonly used to a plurality of radiation imaging apparatuses or a plurality of radiographic image reading apparatuses.

Further, Japanese Patent Application Publication JP-P2003-220054A discloses, in a medical image reading system, to achieve a reduced maintenance work as well as a reduced cost, to enable prompt handling at the time of the occurrence of an error, and to maintain each apparatus constituting the medical image reading system to an optimal state. In the device information collection processing of the above system, a control section in a controller stores error information in regard to the controller, a reservation device and a reading device into an error log information table for each apparatus, adds up an error occurrence frequency for each error item, and makes an error log information indication screen to be displayed on a display section.

However, the medical image reading system as shown in FIG. 1 of JP-P2003-220054A includes only one reading apparatus (radiographic image reading apparatus), and no suggestion is made in regard to application to a general system in which a photostimulable phosphor plate (recording sheet) is commonly used for a plurality of radiation imaging apparatuses or a plurality of radiographic image reading apparatuses.

SUMMARY OF THE INVENTION

The present invention has been achieved in consideration of the above-mentioned problems. It is a first object of the present invention to provide recording sheet usage count evaluation method and apparatus capable of evaluating, even in the case where a plurality of radiation imaging apparatuses and a plurality of radiographic image reading apparatuses exist, a cumulative usage count of a recording sheet for common use in those apparatuses, and capable of reflecting difference in type of the radiographic image reading apparatuses, etc. Further, it is a second object of the present invention to provide a medical information processing apparatus employing such a recording sheet usage count evaluation method.

In order to achieve the aforementioned objects, a recording sheet usage count evaluation method according to one aspect of the present invention is a method of evaluating a usage count of each recording sheet in a radiation imaging system including at least one radiation imaging apparatus for imaging an object by irradiating the object with radiation to record a radiographic image on the recording sheet, at least one radiographic image reading apparatus for reading the radiographic image recorded on the recording sheet to obtain image data, and a plurality of medical image processing apparatuses capable of processing the image data received from the at least one radiographic image reading apparatus, and the method comprises the steps of: (a) receiving, in one medical image processing apparatus, recording sheet identification information for use in identifying the recording sheet, together with the image data obtained by reading the radiographic image recorded on the recording sheet, from the at least one radiographic image reading apparatus; (b) counting, in the one medical image processing apparatus, a usage count number of each recording sheet on a basis of the recording sheet identification information received at step (a), weighting a count value in accordance with a set condition, and accumulating the weighted count value to store the accumulated count value in correspondence with the recording sheet identification information; and (c) calculating, in the one medical image processing apparatus, a total count value for each recording sheet by referring to count values stored in other medical image processing apparatuses and adding the count values in the other medical image processing apparatuses to the count value stored at step (b), in accordance with an operation by an operator and/or a set condition.

Further, a medical image processing apparatus according to one aspect of the present invention is an apparatus for processing image data and evaluating a usage count of each recording sheet and to be used with at least one radiation imaging apparatus for imaging an object by irradiating the object with radiation to record a radiographic image on the recording sheet and at least one radiographic image reading apparatus for reading the radiographic image recorded on the recording sheet to obtain the image data, and the apparatus comprises: reception control means for controlling receiving operation to receive recording sheet identification information for use in identifying the recording sheet, together with the image data obtained by reading the radiographic image recorded on the recording sheet, from the at least one radiographic image reading apparatus; image processing means for processing the image data received under control of the reception control means; counting means for counting a usage count number of each recording sheet on a basis of the recording sheet identification information received under control of the reception control means, weighting a count value in accordance with a set condition, and accumulating the weighted count value to store the accumulated count value into a storage section in correspondence with the recording sheet identification information; and calculating means for calculating a total count value for each recording sheet by referring to count values stored in other medical image processing apparatuses and adding the count values in the other medical image processing apparatuses to the count value stored in the storage section, in accordance with an operation by an operator and/or a set condition.

Still further, a recording sheet usage count evaluation apparatus according to one aspect of the present invention is an apparatus for evaluating a usage count of each recording sheet and to be used with at least one radiation imaging apparatus for imaging an object by irradiating the object with radiation to record a radiographic image on the recording sheet, at least one radiographic image reading apparatus for reading the radiographic image recorded on the recording sheet to obtain image data, and a plurality of medical image processing apparatuses capable of processing the image data received from the at least one radiographic image reading apparatus, and the apparatus comprises: reception control means for controlling receiving operation to receive recording sheet identification information for use in identifying the recording sheet, when the recording sheet identification information is transmitted together with the image data obtained by reading the radiographic image recorded on the recording sheet, from the at least one radiographic image reading apparatus to any one of the plurality of medical image processing apparatuses; and counting means for counting a usage count number of each recording sheet on a basis of the recording sheet identification information received under control of the reception control means, weighting a count value in accordance with a set condition, and accumulating the weighted count value to store the accumulated count value into a storage section in correspondence with the recording sheet identification information.

According to the present invention, by counting the usage count number of each recording sheet, weighting the count value in accordance with a set condition, and accumulating the weighted count value to store the accumulated count value in correspondence with the recording sheet identification information, even in the case where a plurality of radiation imaging apparatuses and a plurality of radiographic image reading apparatuses exist, it becomes possible to evaluate a cumulative usage count of a recording sheet which is commonly used in those apparatuses, and at the time of the evaluation, to reflect difference in type of the radiographic image reading apparatuses, etc.

DESCRIPTION OF THE PREFERRED EMBODIMENTS

Hereinafter, preferred embodiments of the present invention will be described referring to drawings, wherein the same reference numerals are given to the same structural elements, and the description thereof will be omitted.

Figure 1:
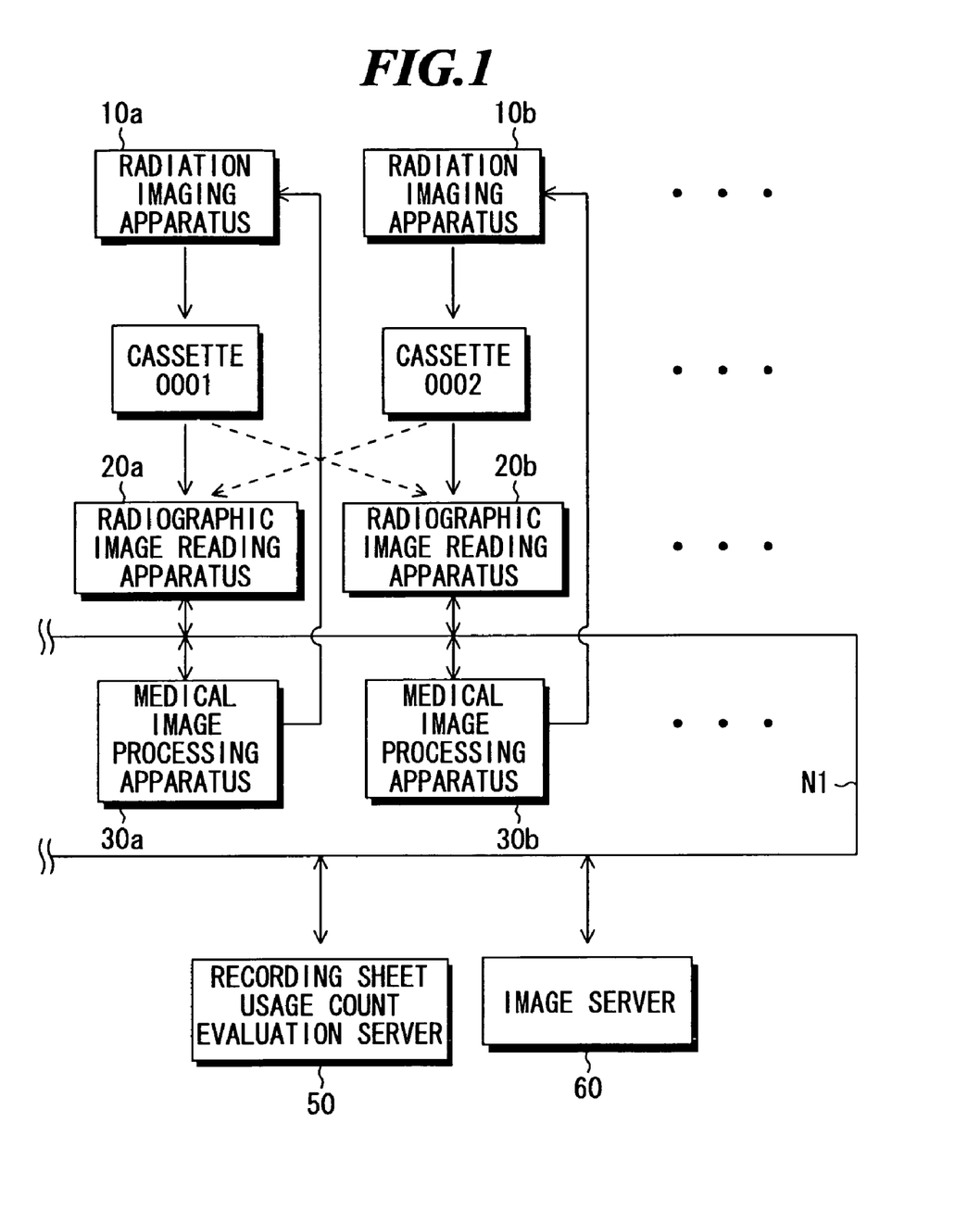
FIG. 1 is a block diagram illustrating a configuration of a radiation imaging system employing a recording sheet usage count evaluation method according to a first embodiment of the present invention.

FIG. 1 is a block diagram illustrating the configuration of a radiation imaging system employing a recording sheet usage count evaluation method according to a first embodiment of the present invention. As shown in FIG. 1, the radiation imaging system includes at least one radiation imaging apparatus (FIG. 1 shows a plurality of radiation imaging apparatuses 10a, 10b, etc.) for imaging an object to be inspected by irradiating the object with radiation to record a radiographic image on a photostimulable phosphor sheet (which is also referred to as "recording sheet" or "imaging plate"), at least one radiographic image reading apparatus (FIG. 1 shows a plurality of radiographic image reading apparatuses 20a, 20b, etc.) for photoelectrically reading information such as radiographic image recorded on the recording sheet to generate image data and image attendant information, and a plurality of medical image processing apparatuses 30a, 30b, etc. for receiving the image data from any one of the radiographic image reading apparatuses, performing a variety of processing of the image data, and displaying or outputting the image.

Each of the medical image processing apparatuses 30a, 30b, etc. processes the image data, and also counts a usage count number of each recording sheet to generate a count value, weights the count value according to a set condition, accumulates the weighted count value, and compares the accumulated count value with a recommended usage count of the recording sheet. Further, the medical image processing apparatuses 30a, 30b, etc. are also used as consoles for controlling the respective radiation imaging apparatuses 10a, 10b, etc., and imaging condition is transmitted and received between each medical image processing apparatus and respective radiation imaging apparatus. Here, the radiographic image reading apparatuses 20a, 20b, etc. and the medical image processing apparatuses 30a, 30b, etc. are connected to each other via a network N1. Further, when necessary, external apparatuses such as a recording sheet usage count evaluation server 50 and an image server 60 are connected to the network N1.

Figure 2:
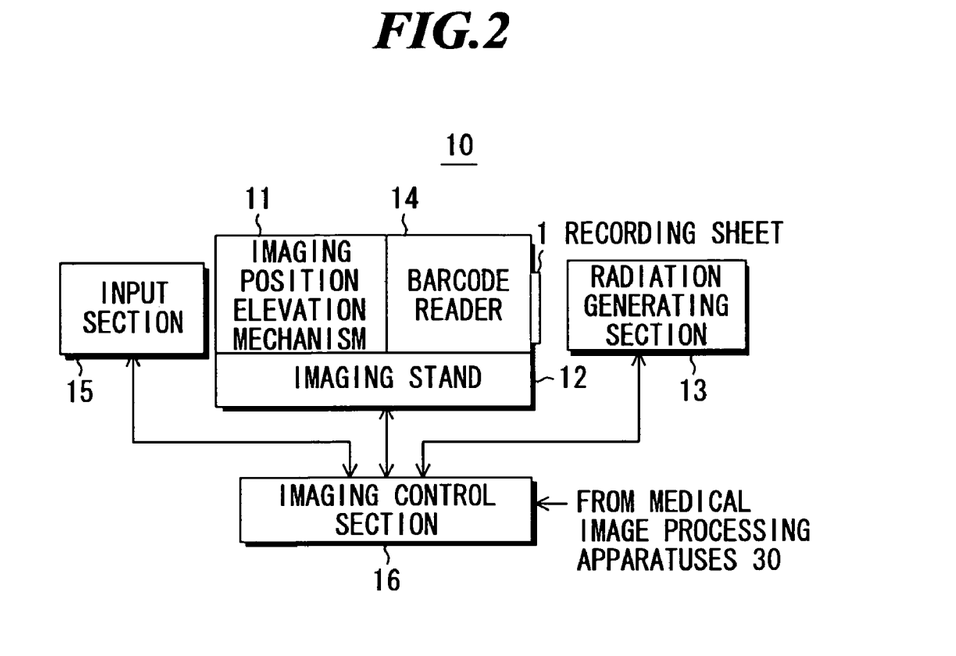
FIG. 2 is a block diagram illustrating the configuration of the radiation imaging apparatus as shown in FIG. 1.

FIG. 2 is a block diagram illustrating the configuration of the radiation imaging apparatus as shown in FIG. 1. The radiation imaging apparatus 10 includes an imaging position elevation mechanism 11 for vertically moving the position of a recording sheet 1 to adjust the imaging position of the object, an imaging stand 12 for positioning the feet of the object, a radiation generating section 13 for irradiating the object with radiation, a barcode reader 14 for reading a barcode attached to the recording sheet 1 as an identification mark, an input section 15 for use in inputting a variety of instructions and imaging conditions, and an imaging control section 16 for controlling the radiation generating section 13, etc. according to the given imaging conditions.

The barcode reader 14 is desirably mounted on the imaging stand 12 so that the barcode on the recording sheet 1 can be read automatically through a window provided on a cassette, when the cassette that contains the recording sheet 1 is set onto the imaging stand 12. However, instead of such fixed mounting, it is possible that the barcode reader 14 is not fixed and the barcode is read manually. Further, the imaging control section 16 is connected to the medical image processing apparatuses, and controls each section based on the signals received from the medical image processing apparatuses.

The recording sheet 1 for use in the radiation imaging is a sheet having a photostimulable phosphor substance coated thereon, on which the information of the object is recorded when irradiated with radiation through the object. The radiation imaging of the object is performed under predetermined imaging conditions, and the resultant radiographic image is recorded on the recording sheet 1. After imaging, the recording sheet 1 is set on any one of the radiographic image reading apparatuses.

Figure 3:
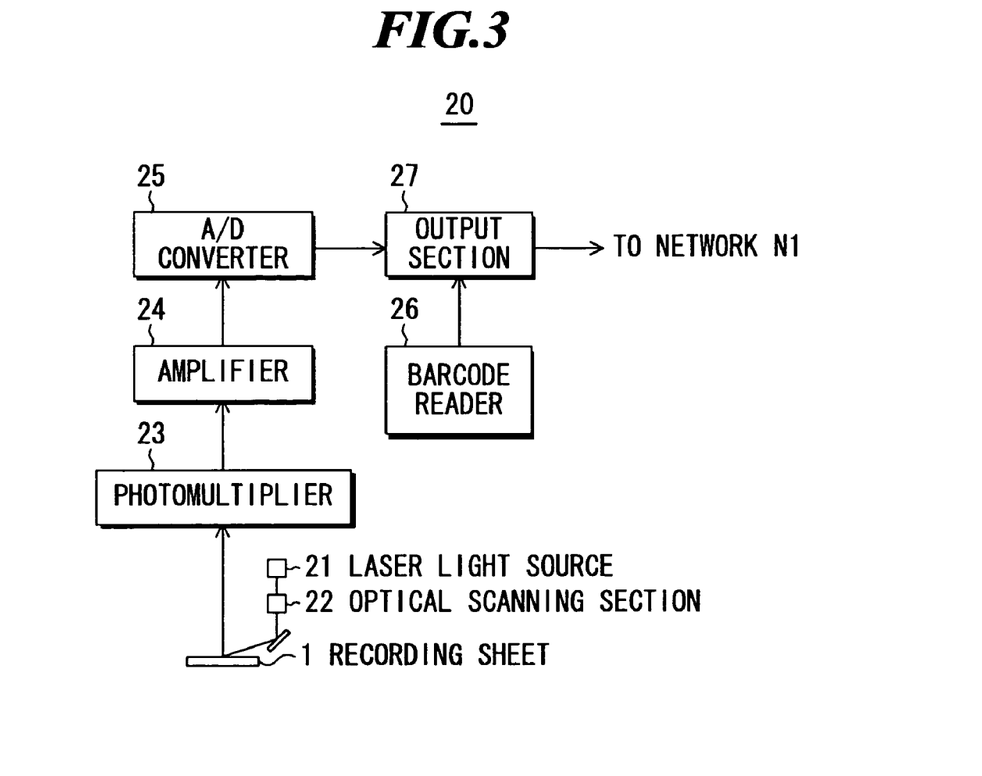
FIG. 3 is a block diagram illustrating the configuration of the radiographic image reading apparatus as shown in FIG. 1.

FIG. 3 is a block diagram illustrating the configuration of the radiographic image reading apparatus as shown in FIG. 1. In the radiographic image reading apparatus 20 as shown in FIG. 3, a light beam output from a laser light source 21 scans the surface of the recording sheet 1 through an optical scanning section 22. By the scanning, the recording sheet 1 is irradiated with the light beam, and from an area irradiated with the light beam, there is produced stimulated fluorescent light, quantity of which depends on the recorded and stored radiographic image information. The stimulated fluorescent light is photoelectrically detected by a photomultiplier (photoelectron multiplier) 23, so that an analog signal is output therefrom, amplified in an amplifier 24, and then digitized in an A/D converter 25. Also, the barcode attached to the recording sheet 1 is read by a barcode reader 26, and the barcode information is used as image attendant information corresponding to patient information and examination information. The image data and the barcode information thus generated are transmitted from an output section 27 to the medical image processing apparatus via the network N1.

Figure 4:
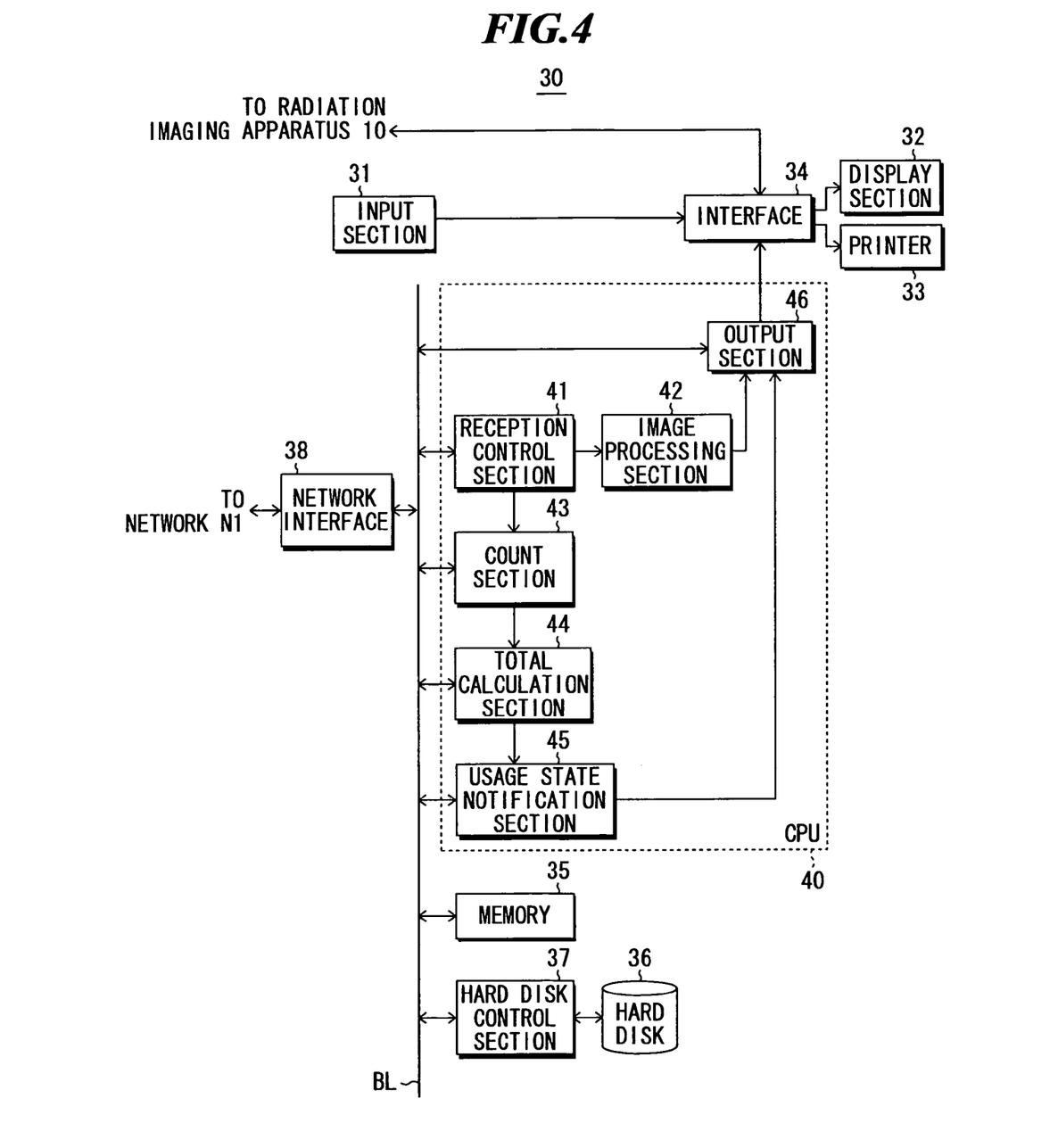
FIG. 4 is a block diagram illustrating the configuration of a medical image processing apparatus according to the first embodiment of the present invention.

FIG. 4 is a block diagram illustrating the configuration of the medical image processing apparatus according to the first embodiment of the present invention. The medical image processing apparatus 30 includes an input section 31 such as a keyboard or a mouse, for inputting a variety of instructions, etc., a display section 32 such as a CRT display, for displaying an image, a printer 33 for printing an image on a film, etc., an interface 34 to which the input section 31 to the printer 33 are connected, a memory 35 for temporarily storing the image data and the image attendant information received from the radiographic image reading apparatus, a hard disk 36, a hard disk controller 37, a network interface 38, and a central processing unit (hereinafter referred to as CPU) 40. The units from the memory 35 to the CPU 40 are connected to each other via a bus line BL.

In the hard disk 36, software (control program) for actuating the CPU 40 is stored. Here, as a recording medium for storing the control program, external hard disk, flexible disk, MO, MT, RAM, CD-ROM, DVD-ROM or the like may be used as well as the built-in hard disk 36. As functional blocks, a reception control section 41, an image processing section 42, a count section 43, a total calculation section 44, a usage state notification section 45 and an output section 46 are configured by means of the CPU 40 and the software (control program).

The reception control section 41 controls reception operation so as to receive, from any one of the radiographic image reading apparatuses, the image data obtained by reading the radiographic image recorded on the recording sheet and recording sheet identification information for use in identifying the recording sheet. In the present embodiment, as the recording sheet identification information, the barcode information generated in the radiographic image reading apparatus is used. Further, the image processing section 42 performs image processing such as gradation processing or space frequency processing onto the image data received under the control of the reception control section 41.

The count section 43 counts a usage count number of each recording sheet on the basis of the recording sheet identification information received under the control of the reception control section 41, weights a count value according to a set condition, accumulates the weighted count value, and stores the accumulated count value into a storage section such as the memory 35, the hard disk 36 or the like on correspondence with the recording sheet identification information.

The recording sheet has a laminate structure including a reflective layer, a phosphor layer and a protection layer formed on a base layer of a polyethylene terephthalate material having a thickness of 0.2 mm or on that order, among which the phosphor layer occupies a principal portion in the thickness. Accordingly, the recording sheet has a characteristic being gradually degraded by scratches and folds caused by running or being bent through the transfer path of the radiographic image reading apparatus. Here, the degree of degradation in the recording sheet characteristic varies depending on the factors including difference in type of the radiographic image reading apparatuses, difference in installation environment of the radiographic image reading apparatuses and difference in manufacturing time of the recording sheets. Therefore, the weighting condition is set based on at least one of the above factors.

For example, since the length of the transfer path, the number of bends, the bending direction or the bending angle of the recording sheet is different depending on the type of the radiographic image reading apparatus, the weighting condition may be set corresponding to such matters, or the weighting condition may be set simply corresponding to the type of the apparatus. Also, since the temperature or the humidity inside the radiographic image reading apparatus differs depending on the installation environment of the radiographic image reading apparatus, the weighting condition may be set corresponding to such matters. Further, since the manufacturing time or the manufacturing line differs in the recording sheet to be used, the weighting condition may be set corresponding to such matters. Alternatively, the weighting condition may be set in correspondence with combination of two or more of the above matters.

The total calculation section 44 refers to the count values stored in other medical image processing apparatuses and adding the count values in other medical image processing apparatuses to the count value stored in the storage section to calculate the total count value for each recording sheet, according to an operation by an operator or a set condition.

The usage state notification section 45 compares the total count value calculated by the total calculation section 44 with a set recommended usage count of the recording sheet, and thus obtains a comparison result. The recommended usage count of the recording sheet is set based on, for example, a recommended usage count (useful count number) described in the product specification, or the like, of the recording sheet provided by the recording sheet manufacturing company. Further, based on the obtained comparison result, the usage state notification section 45 generates a signal for notifying of the usage state of each recording sheet by image or voice, and outputs the above signal to the output section 46.

The output section 46 outputs the image data, on which image processing is performed by the image processing section 42, onto the display section 32 or the printer 33 via the interface 34. Thereby, the radiographic image is displayed on the screen of the display section 32, or printed on a film, etc. Also, based on the signal input from the usage state notification section 45, the output section 46 outputs an image signal or a voice signal to the display section 32 via the interface 34 the output section 46 to make the display section 32 indicate the usage state of each recording sheet by image or voice. Accordingly, the usage state of each recording sheet is notified by image or voice at the display section 32.

In the present embodiment, although the units from the reception control section 41 to the output section 46 are configured by means of the CPU and the software, it may be possible to configure them by using a digital circuit and an analog circuit.

Figure 5:
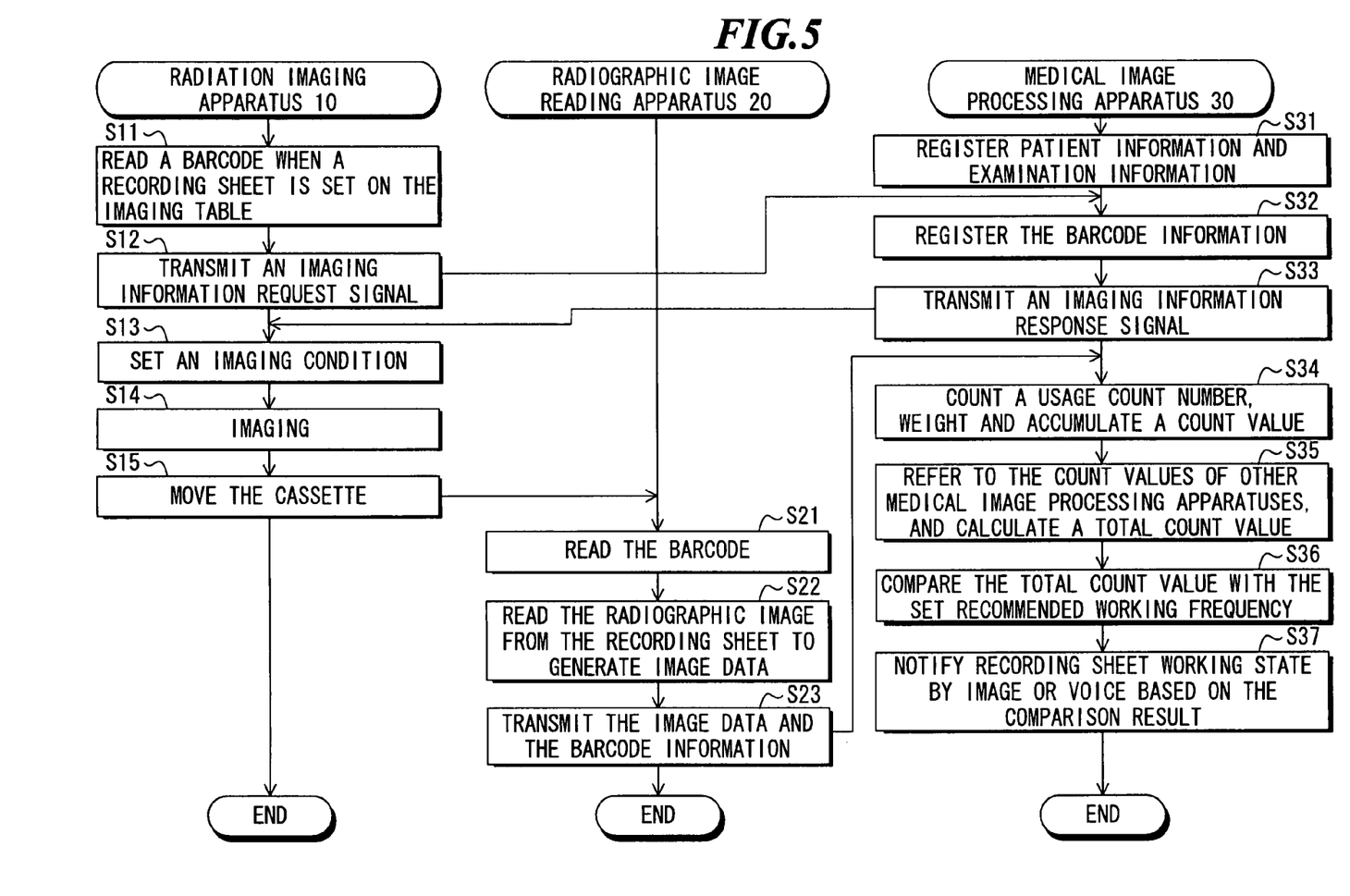
FIG. 5 is a flowchart illustrating a recording sheet usage count evaluation method according to the first embodiment of the present invention.

Next, the recording sheet usage count evaluation method according to the first embodiment of the present invention will be described, referring to FIGS. 1-7. FIG. 5 is a flowchart illustrating the recording sheet usage count evaluation method according to the first embodiment of the present invention.

As shown in FIG. 5, at first, the registration of an imaging object is performed in the medical image processing apparatus 30. Namely, at step S31, patient information and examination information such as an imaging menu and an imaging condition are registered. In ordinary imaging, a plurality of times of imaging is performed at a time, and therefore, patient information and examination information for a plurality of times of imaging are collectively registered.

At the time of radiation imaging, at step S11, when the operator sets a cassette containing a recording sheet 1 on the imaging stand 12 of the radiation imaging apparatus 10, the barcode reader 14 reads the barcode being attached to the recording sheet 1 as identification mark. At step S12, the radiation imaging apparatus 10 transmits to the medical image processing apparatus 30 an imaging information request signal including the barcode information that is obtained by reading the barcode of the recording sheet 1, so as to request the patient information and the examination information in regard to the imaging in which the above recording sheet 1 is used. In the present embodiment, although the barcode reader 14 is connected to the imaging control section 16 of the radiation imaging apparatus 10, the barcode reader 14 may be directly connected to the medical image processing apparatus 30 through a wired or a wireless link.

At step S32, the medical image processing apparatus 30 registers the barcode information included in the received imaging information request signal, in association with the patient information and the examination information in regard to the imaging at this time, and then, transmits an imaging information response signal including the patient information and the examination information concerned to the radiation imaging apparatus 10 at step S33.

At step S13, the radiation imaging apparatus 10 sets the imaging condition based on the examination information included in the received imaging information response signal. Further, at step S14, radiation imaging is performed under the set imaging condition. Thereafter, at step S15, the operator removes the cassette set on the imaging stand 12 of the radiation imaging apparatus 10, and transfers the cassette to the radiographic image reading apparatus 20.

In the radiation imaging, generally, it is not fixed which recording sheet is used in which radiation imaging apparatus. Also, as shown in FIG. 1, the cassette containing the recording sheet of No. 0001 on which imaging has been completed by the radiation imaging apparatus 10a may be set to the radiographic image reading apparatus 20a or the radiographic image reading apparatus 20b. Similarly, the cassette containing the recording sheet of No. 0002 on which imaging has been completed by the radiation imaging apparatus 10b may be set to the radiographic image reading apparatus 20b or the radiographic image reading apparatus 20a.

Again, referring to FIG. 5, at step S21, the radiographic image reading apparatus 20 reads the barcode attached to the recording sheet, and at step S22, generates image data by reading the radiographic image recorded on the recording sheet. Thereafter, at step S23, the radiographic image reading apparatus 20 transmits the barcode information together with the image data, to the medical image processing apparatus 30.

The reception control section 41 in the medical image processing apparatus 30 controls receiving operation so as to receive the barcode information together with the image data from the radiographic image reading apparatus 20. The barcode information is used as recording sheet identification information for identifying the recording sheet. Since the barcode information is associated with the patient information and the examination information in advance, it is possible to associate the image data, that is received together with the barcode information, with the patient information and the examination information. Alternatively, as means for identifying the recording sheet, it is possible to use an RFID tag or a size of the recording sheet other than the barcode. For example, when there is only one recording sheet of special size, the recording sheet can be identified by the size of the recording sheet.

At step S34, the count section 43 in the medical image processing apparatus 30 counts a usage count number of each recording sheet on the basis of the recording sheet identification information received under the control of the reception control section 41 to generate a count value, weights the count value according to a set condition, accumulates the weighted count value, and stores the accumulated count value into a storage section such as the memory 35 and the hard disk 36, in correspondence with the recording sheet identification information. Here, the count section 43 may count a usage count number of each recording sheet for each radiographic image reading apparatus, weights the count value according to a set condition, accumulates the weighted count value, and stores the accumulated count value into the storage section in correspondence with the recording sheet identification information.

Figure 6:
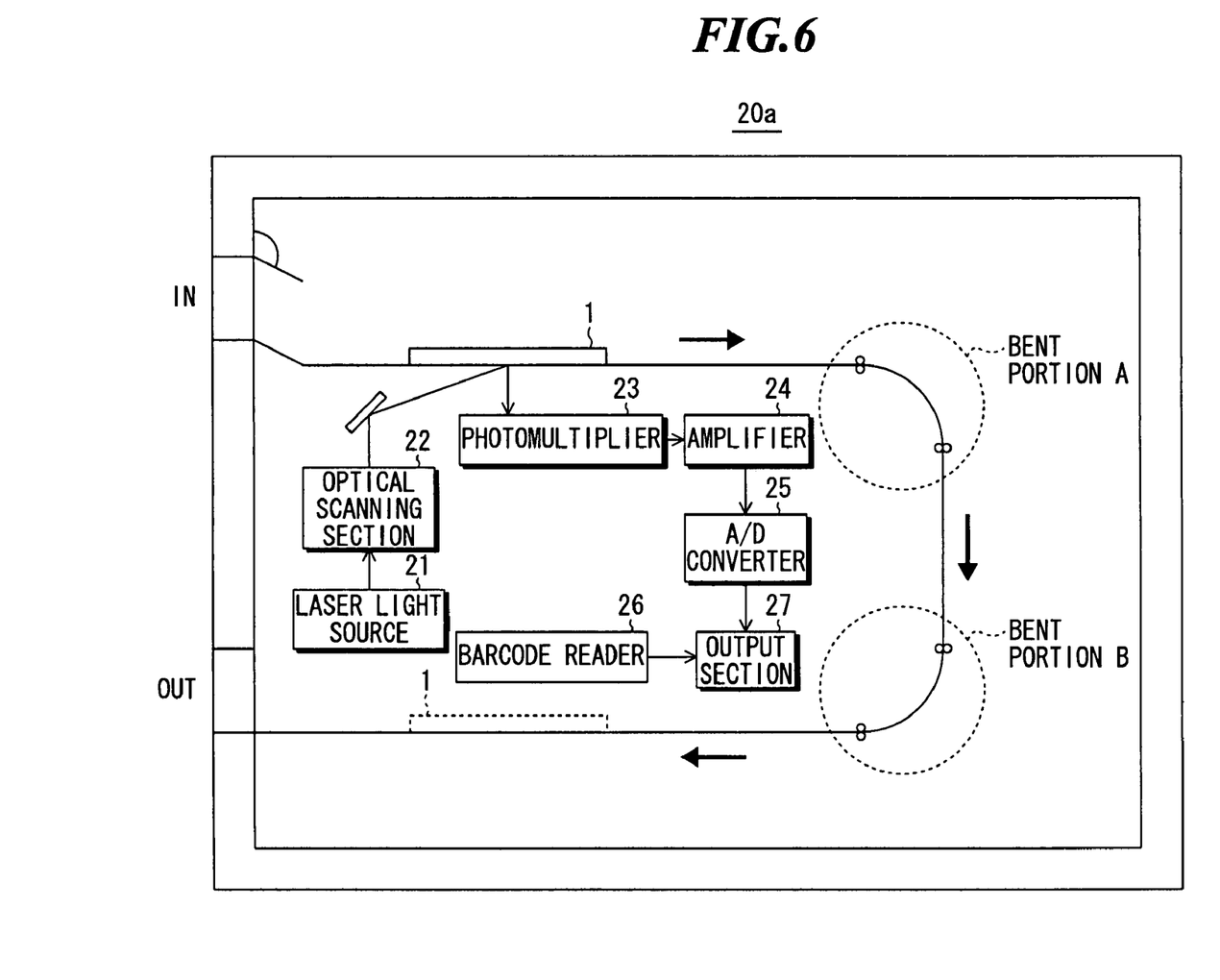
FIG. 6 is a diagram illustrating an example of a transfer path in a first radiographic image reading apparatus.

FIG. 6 is a diagram illustrating an example of a transfer path in a first radiographic image reading apparatus. In the first radiographic image reading apparatus 20a, the length of the transfer path is approximately 1 meter, and the recording sheet inserted from an input section IN is transferred to an output section OUT via a bent portion A and a bent portion B. At the bent portion A and the bent portion B, the recording sheet is bent in the same direction.

Figure 7:
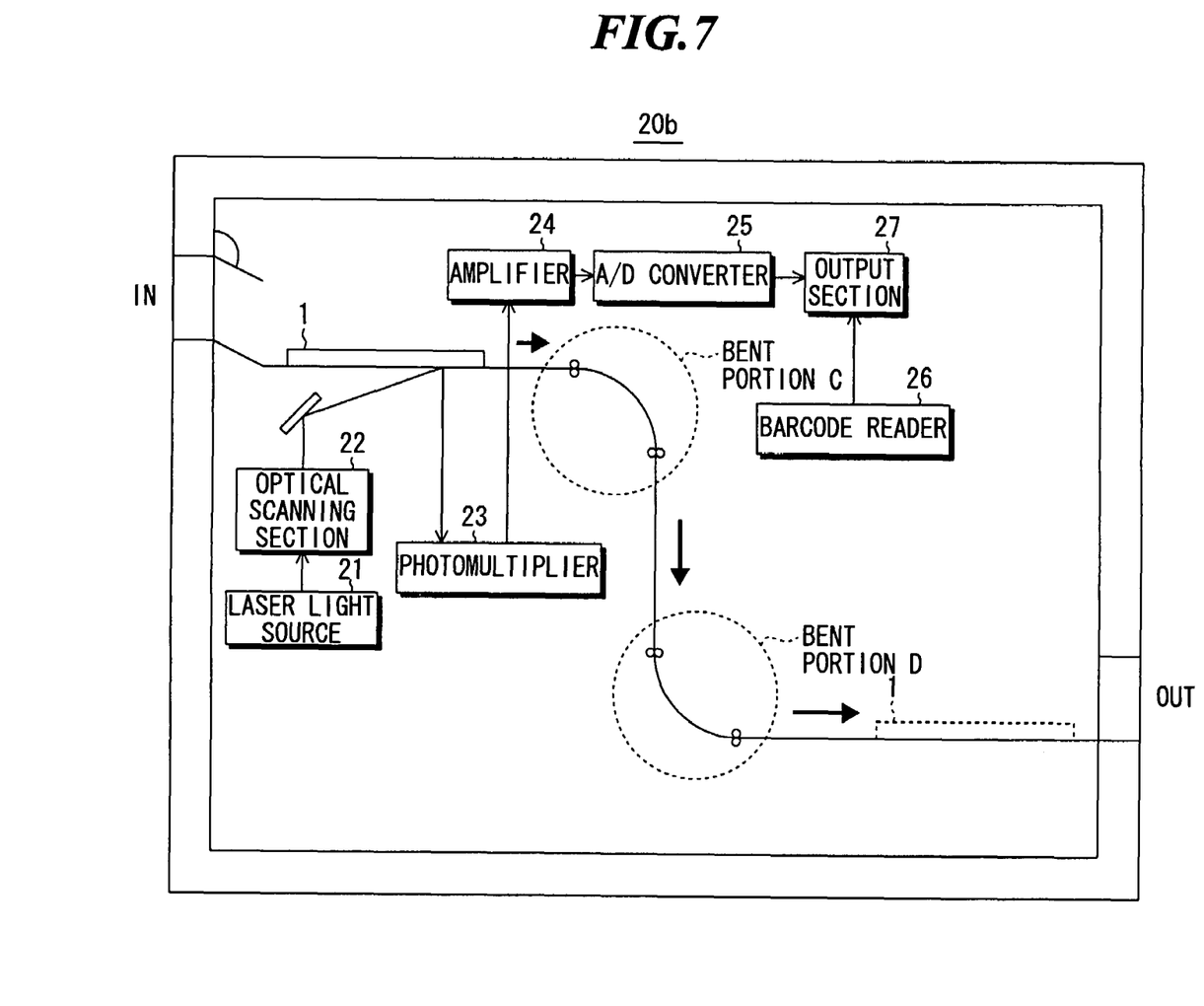
FIG. 7 is a diagram illustrating an example of a transfer path in a second radiographic image reading apparatus.

FIG. 7 is a diagram illustrating an example of a transfer path in a second radiographic image reading apparatus. In the second radiographic image reading apparatus 20b, the length of the transfer path is approximately 1 meter, and the recording sheet inserted from an input section IN is transferred to an output section OUT via a bent portion C and a bent portion D. At the bent portion C and the bent portion D, the recording sheet is bent in the opposite directions.

In the present embodiment, using as a criterion the transfer path of the radiographic image reading apparatus 20a as shown in FIG. 6, weighting factors are respectively set in proportion to the length of the transfer path, the number of bends and the bending angle. Further, in the case of the opposite bending directions, the degree of degradation in the recording sheet characteristic is large as compared with the case of the same bending direction, and therefore, the weighting factors in regard to the number of bends are set 1.5 times as large. In the following, for the sake of simple explanation, the weighting factor of the radiographic image reading apparatus 20a is set at "1", while the weighting factor of the radiographic image reading apparatus 20b is set at "1.5".

For example, when the medical image processing apparatus 30a as shown in FIG. 1 receives image data obtained from a recording sheet of No. 0001 from the radiographic image reading apparatus 20a for the first time, the medical image processing apparatus 30a sets a count value $C_1(30a)$ at "1" in regard to the recording sheet of No. 0001. Thereafter, when the medical image processing apparatus 30a receives image data obtained from the recording sheet of No. 0001 from the radiographic image reading apparatus 20a, the medical image processing apparatus 30a sets the count value $C_1(30a)$ at "2" in regard to the recording sheet of No. 0001. On the other hand, when the medical image processing apparatus 30a receives image data obtained from the recording sheet of No. 0001 from the radiographic image reading apparatus 20b, the medical image processing apparatus 30a sets the count value $C_1(30a)$ at "2.5" in regard to the recording sheet of No. 0001. Alternatively, medical image processing apparatus 30a may count a usage count number of each recording sheet in regard to the radiographic image reading apparatuses 20a, 20b, etc. to obtain count values $C_1(20a, 30a)$, $C_1(20b, 30a)$, etc.

At step S35, the total calculation section 44 in the medical image processing apparatus 30 refers to count values stored in other medical image processing apparatuses and adding the count values in other medical image processing apparatuses to the count value stored in the storage section in accordance with an operation by an operator or a set condition, so as to calculate a total count value for each recording sheet.

For example, the medical image processing apparatus 30a as shown in FIG. 1 accesses the other medical image processing apparatuses 30b, etc. through the network N1, and requests the count values of the recording sheet working frequencies. In response to the above request, the other medical image processing apparatuses 30b, etc. being requested to send the count values of the recording sheet working frequencies transmit the count values to the medical image processing apparatus 30a. Thereby, the medical image processing apparatus 30a can obtain the count values retained in the other medical image processing apparatuses.

Here, information related to the other medical image processing apparatuses, which information includes information on the type name and the address thereof, is registered beforehand by employing the hard disk etc. in each medical image processing apparatus. The above registration may be performed automatically via the network N1, or manually by the operator, or by using a portable recording medium such as a floppy (registered trademark) disk. In the case where the other medical image processing apparatuses 30b, etc. are not activated, the total calculation section 44 in the medical image processing apparatus 30a indicates a communication error onto the display section 32, or accesses the other medical image processing apparatuses again after a lapse of time.

The total calculation section 44 in the medical image processing apparatus 30a adds, for example, the count values $C_1(30b)$, etc. for the recording sheet of No. 0001 in regard to the medical image processing apparatuses 30b, etc. to the count value $C_1(30a)$ for the recording sheet of No. 0001 in regard to the medical image processing apparatus 30a, and thereby calculates a total count value $S_1=C_1(30a)+C_1(30b)+\ldots$ for the recording sheet of No. 0001.

Alternatively, the medical image processing apparatus 30a may calculate the total count values for each recording sheet in regard to the respective radiographic image reading apparatuses 20a, 20b, etc.: $S_N(20a)=C_N(20a, 30a)+C_N(20a, 30b)+\ldots$, $S_N(20b)=C_N(20b, 30a)+C_N(20b, 30b)+\ldots$, and so on. Further, the medical image processing apparatus 30a calculates the total count value for the entire radiographic image reading apparatuses: $S_N=S_N(20a)+S_N(20b)+\ldots$.

Additionally, resets of the total count values in the above medical image processing apparatuses 30a, 30b, etc. are performed simultaneously. Further, it is possible by a system setting to modify whether or not the total count value is resettable, and in the initial setting, "not resettable" is specified.

At step S36, the usage state notification section 45 in the medical image processing apparatus 30 compares the total count value $S_N$ calculated by the total calculation section 44 with the set recommended usage count of the recording sheet, and thus obtains a comparison result.

At step S37, based on the obtained comparison result, the usage state notification section 45 generates a signal for notifying of a usage state of each recording sheet by image or voice, and outputs the signal to the output section 46. Based on the signal from the usage state notification section 45, the output section 46 outputs an image signal or a voice signal onto the display section 32 via the interface 34, and thereby makes the display section 32 indicate the usage state of each recording sheet by image or voice. Thereby, the usage state of each recording sheet is notified at the display section 32 by image or voice.

Here, the notification of the recording sheet usage state may be performed when the count value of the recording sheet exceeds the recommended usage count of the recording sheet, or for example, when the count value of the recording sheet becomes 90% of the recommended usage count of the recording sheet. Further, the display of the recording sheet usage state may be performed in an ordinary image processing, without displaying a screen of dedicated use.

According to the present embodiment, in the medical image processing apparatus, the usage count of each recording sheet can be evaluated with weighting, and thus, it is possible to maintain the radiographic image quality by discarding worn-out recording sheets based on the evaluation result. Further, it is possible to grasp a proper time to exchange the recording sheet.

Next, the medical image processing apparatus according to a second embodiment of the present invention will be described.

Figure 8:
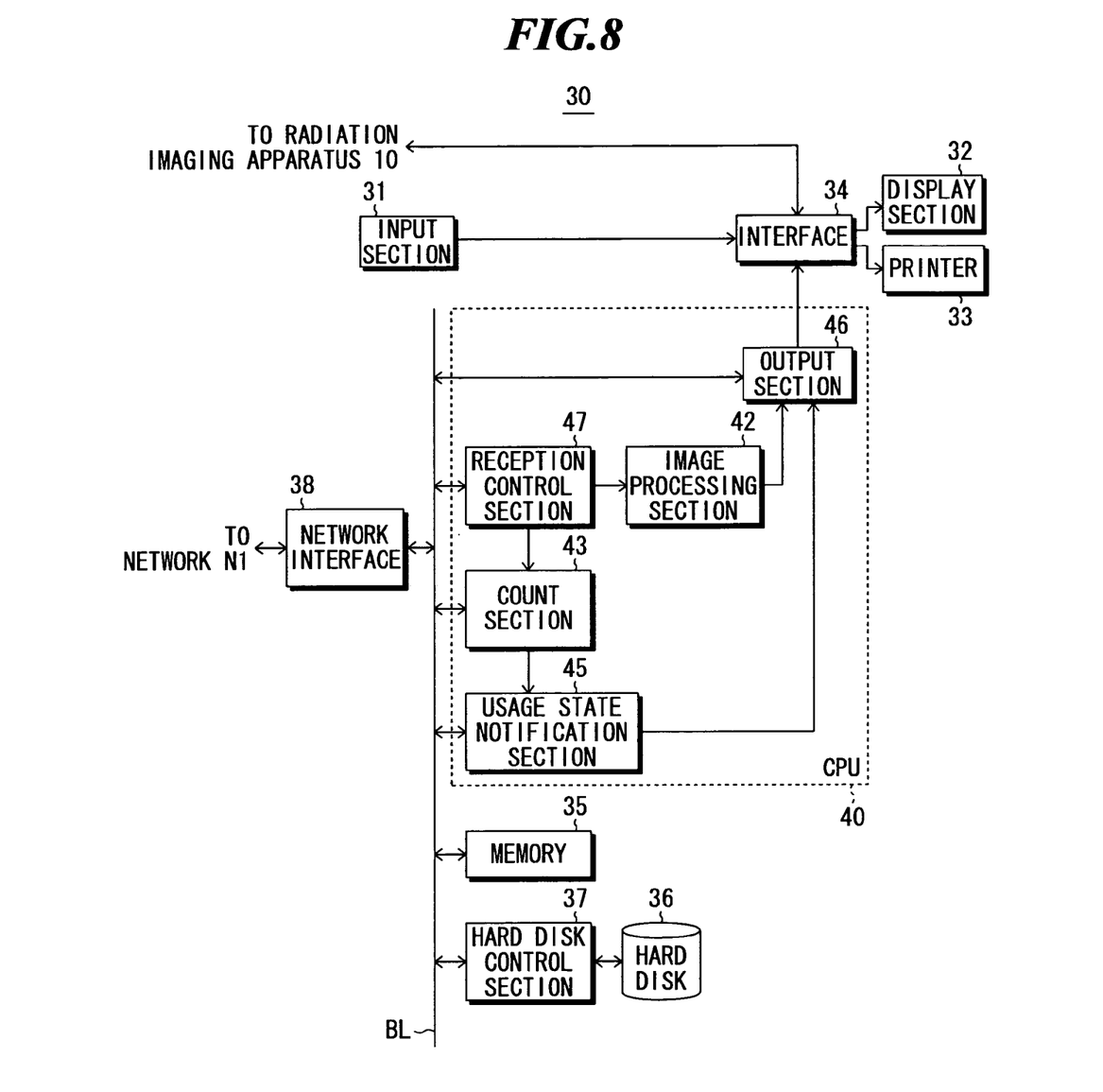
FIG. 8 is a block diagram illustrating a configuration of a medical image processing apparatus according to a second embodiment of the present invention.

FIG. 8 is a block diagram illustrating the configuration of a medical image processing apparatus according to the second embodiment of the present invention. In the medical image processing apparatus of the present embodiment, the reception control section 41 in the medical image processing apparatus of the first embodiment as shown in FIG. 4 is replaced with a reception control section 47, and the function of the total calculation section 44 is removed.

As shown in FIG. 8, in the medical image processing apparatus 30, there are configured a reception control section 47, an image processing section 42, a count section 43, a usage state notification section 45 and an output section 46 by means of the CPU 40 and software (control program). When image data and recording sheet identification information are transmitted from any one of the radiographic image reading apparatuses to any one of the medical image processing apparatuses, the reception control section 47 controls receiving operation to receive the recording sheet identification information.

On receipt of the image data transmitted to the medical image processing apparatus 30, the image processing section 42 processes the image data. The count section 43 counts a usage count number of each recording sheet on the basis of the recording sheet identification information received under the control of the reception control section 47, weights a count values according to a set condition, accumulates the weighted count value, and stores the accumulated count value into a storage section such as the memory 35, the hard disk 36 or the like, in correspondence with the recording sheet identification information.

The usage state notification section 45 compares the count value stored in the storage section by the count section 43 with a set recommended usage count of the recording sheet, and thus obtains a comparison result. Further, based on the obtained comparison result, the usage state notification section 45 generates a signal for notifying of the usage state of each recording sheet by image or voice, and outputs the signal to the output section 46.

the output section 46 outputs an image signal or a voice signal to the display section 32 via the interface 34 based on the signal from the usage state notification section 45, so as to make the display section 32 indicate the usage state of each recording sheet by image or voice. Thereby, the usage state of each recording sheet is notified by image or voice at the display section 32.

Also in the present embodiment, it is possible that the count section 43 counts a usage count number of each recording sheet for each radiographic image reading apparatus, weights the count values according to a set condition, accumulates the weighted count value, and stores the accumulated count value into the storage section in correspondence with the recording sheet identification information, such that the usage state of each recording sheet may be evaluated for each radiographic image reading apparatus.

According to the present embodiment, when image data and recording sheet identification information are transmitted from any one of the radiographic image reading apparatuses to any one of the medical image processing apparatuses, each medical image processing apparatus receives the recording sheet identification information and counts up a usage count number while weighting the count value to accumulate the weighted count value, and thereby, the usage state of each recording sheet can be evaluated or notified.

Next, a recording sheet usage count evaluation apparatus according to one embodiment of the present invention will be described. In the present embodiment, instead of evaluating the recording sheet usage count by means of the medical image processing apparatuses 30a, 30b, etc. as shown in FIG. 1, a recording sheet usage count evaluation server 50 is separately provided as a recording sheet usage count evaluation apparatus.

Figure 9:
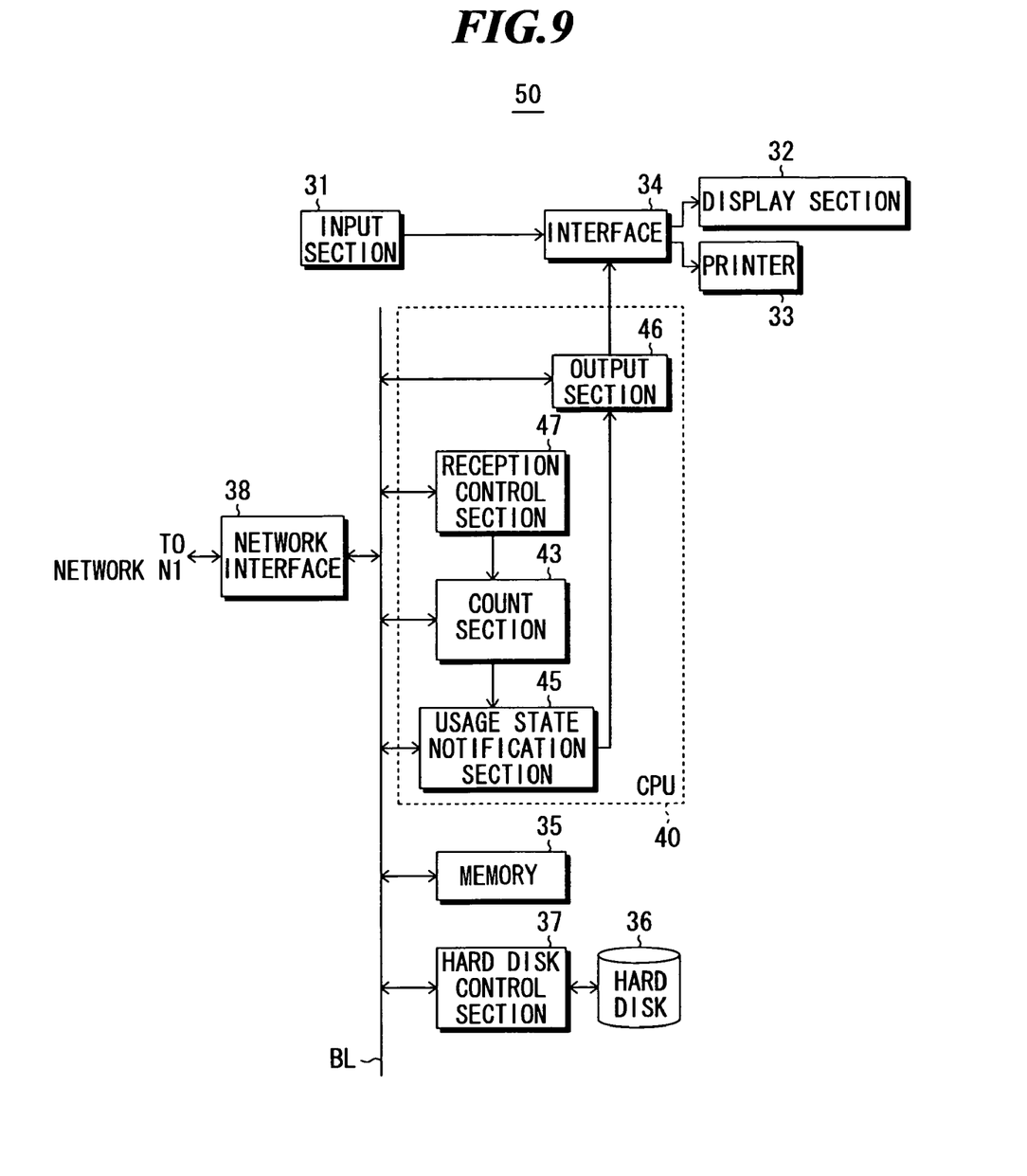
FIG. 9 is a block diagram illustrating a configuration of a recording sheet usage count evaluation server according to one embodiment of the present invention.

FIG. 9 is a block diagram illustrating the configuration of a recording sheet usage count evaluation server according to one embodiment of the present invention. The recording sheet usage count evaluation server 50 is an apparatus in which the function of the image processing section 42 is removed from the medical image processing apparatus 30 as shown in FIG. 8. Further, the recording sheet usage count evaluation server 50 may further have a function as an image server such that image data, patient information and so on are stored into the hard disk 36.

As shown in FIG. 9, in the recording sheet usage count evaluation server 50, there are configured a reception control section 47, a count section 43, a usage state notification section 45 and an output section 46 by means of the CPU 40 and the software (control program). When image data and recording sheet identification information are transmitted from any one of the radiographic image reading apparatuses to any one of the medical image processing apparatuses, the reception control section 47 controls receiving operation to receive the recording sheet identification information.

The count section 43 counts a usage count number of each recording sheet on the basis of the recording sheet identification information received under the control of the reception control section 47 to generate a count value, weights the count value according to a set condition, accumulates the weighted count value, and stores the accumulated count value into a storage section such as the memory 35, the hard disk 36 or the like, in correspondence with the recording sheet identification information.

The usage state notification section 45 compares the count value stored in the storage section by the count section 43 with the set recommended usage count of the recording sheet, and thus obtains a comparison result. Further, based on the obtained comparison result, the usage state notification section 45 generates a signal for notifying of the usage state of each recording sheet by image or voice, and outputs the above signal to the output section 46.

The output section 46 outputs an image signal or a voice signal to the display section 32 via the interface 34 based on the signal input from the usage state notification section 45, so as to make the display section 32 indicate the usage state of each recording sheet by image or voice. Thereby, the usage state of each recording sheet is notified by image or voice at the display section 32.

Also in the present embodiment, the count section 43 counts a usage count number on a basis of each recording sheet for each radiographic image reading apparatus, weights the count value according to a set condition, accumulates the weighted count value, and stores the accumulated count value into the storage section in correspondence with the recording sheet identification information, and thereby, the usage state of each recording sheet may be evaluated for each radiographic image reading apparatus.

According to the present embodiment, when the image data and the recording sheet identification information are transmitted from any one of the radiographic image reading apparatuses to any one of the medical image processing apparatuses, the recording sheet usage count evaluation server receives the recording sheet identification information and counting a usage count number while weighting the count value, and therefore, is possible to evaluate or notify of the usage state of each recording sheet.

The invention claimed is:

1. A recording sheet usage count evaluation method of evaluating a usage count of each recording sheet in a radiation imaging system including at least one radiation imaging apparatus for imaging an object by irradiating the object with radiation to record a radiographic image on the recording sheet, at least one radiographic image reading apparatus for reading the radiographic image recorded on the recording sheet to obtain image data, and a plurality of medical image processing apparatuses capable of processing the image data received from said at least one radiographic image reading apparatus, said method comprising the steps of:
    (a) receiving, in one medical image processing apparatus, recording sheet identification information for use in identifying the recording sheet, together with the image data obtained by reading the radiographic image recorded on the recording sheet, from said at least one radiographic image reading apparatus;
    (b) counting, in said one medical image processing apparatus, a usage count number of each recording sheet on a basis of the recording sheet identification information received at step (a), weighting a count value in accordance with a set condition reflecting a degree of degradation in a characteristic of the recording sheet, and accumulating the weighted count value to store the accumulated count value in correspondence with the recording sheet identification information; and
    (c) calculating, in said one medical image processing apparatus, a total count value for each recording sheet by referring to count values stored in other medical image processing apparatuses and adding the count values in said other medical image processing apparatuses to the count value stored at step (b), in accordance with an operation by an operator and/or a set condition.

2. The recording sheet usage count evaluation method according to claim 1, wherein step (b) includes weighting the count value in accordance with at least one of a condition set for each radiographic image reading apparatus, a condition set for each installation environment of the radiographic image reading apparatus, and a condition set for each recording sheet.

3. The recording sheet usage count evaluation method according to claim 1, further comprising the steps of:
    (d) obtaining, in said one medical image processing apparatus, a comparison result by comparing the total count value calculated at step (c) with a set recommended usage count of the recording sheet; and
    (e) notifying, in said one medical image processing apparatus, of a usage state of each recording sheet by image and/or voice on a basis of the comparison result obtained at step (d).

4. A recording sheet usage count evaluation method of evaluating a usage count of each recording sheet in a radiation imaging system including at least one radiation imaging apparatus for imaging an object by irradiating the object with radiation to record a radiographic image on the recording sheet, at least one radiographic image reading apparatus for reading the radiographic image recorded on the recording sheet to obtain image data, and a plurality of medical image processing apparatuses capable of processing the image data received from said at least one radiographic image reading apparatus, said method comprising the steps of:

(a) receiving, in one medical image processing apparatus, recording sheet identification information for use in identifying the recording sheet, when the recording sheet identification information is transmitted together with the image data obtained by reading the radiographic image recorded on the recording sheet, from said at least one radiographic image reading apparatus to any one of said plurality of medical image processing apparatuses; and (b) counting, in said one medical image processing apparatus, a usage count number of each recording sheet on a basis of the recording sheet identification information received at step (a), weighting a count value in accordance with a set condition reflecting a degree of degradation in a characteristic of the recording sheet, and accumulating the weighted count value to store the accumulated count value in correspondence with the recording sheet identification information.

5. The recording sheet usage count evaluation method according to claim 4, wherein step (b) includes weighting the count value in accordance with at least one of a condition set for each radiographic image reading apparatus, a condition set for each installation environment of the radiographic image reading apparatus, and a condition set for each recording sheet.

6. The recording sheet usage count evaluation method according to claim 4, further comprising the steps of:

(c) obtaining, in said one medical image processing apparatus, a comparison result by comparing the count value stored at step (b) with a set recommended usage count of the recording sheet; and (d) notifying, in said one medical image processing apparatus, of a usage state of each recording sheet by image and/or voice on a basis of the comparison result obtained at step (c).

7. A medical image processing apparatus for processing image data and evaluating a usage count of each recording sheet and to be used with at least one radiation imaging apparatus for imaging an object by irradiating the object with radiation to record a radiographic image on the recording sheet and at least one radiographic image reading apparatus for reading the radiographic image recorded on the recording sheet to obtain the image data, said apparatus comprising:

reception control means for controlling receiving operation to receive recording sheet identification information for use in identifying the recording sheet, together with the image data obtained by reading the radiographic image recorded on the recording sheet, from said at least one radiographic image reading apparatus;

image processing means for processing the image data received under control of said reception control means;

counting means for counting a usage count number of each recording sheet on a basis of the recording sheet identification information received under control of said reception control means, weighting a count value in accordance with a set condition reflecting a degree of degradation in a characteristic of the recording sheet, and accumulating the weighted count value to store the accumulated count value into a storage section in correspondence with the recording sheet identification information; and calculating means for calculating a total count value for each recording sheet by referring to count values stored in other medical image processing apparatuses and adding the count values in said other medical image processing apparatuses to the count value stored in the storage section, in accordance with an operation by an operator and/or a set condition.

8. The medical image processing apparatus according to claim 7, wherein said counting means weights the count value in accordance with at least one of a condition set for each radiographic image reading apparatus, a condition set for each installation environment of the radiographic image reading apparatus, and a condition set for each recording sheet.

9. The medical image processing apparatus according to claim 7, further comprising:

notification means for obtaining a comparison result by comparing the total count value calculated by said calculating means with a set recommended usage count of the recording sheet, and notifying of a usage state of each recording sheet by image and/or voice on a basis of the obtained comparison result.

10. A medical image processing apparatus for processing image data and evaluating a usage count of each recording sheet and to be used with at least one radiation imaging apparatus for imaging an object by irradiating the object with radiation to record a radiographic image on the recording sheet and at least one radiographic image reading apparatus for reading the radiographic image recorded on the recording sheet to obtain the image data, said apparatus comprising:

reception control means for controlling receiving operation to receive recording sheet identification information for use in identifying the recording sheet, when the recording sheet identification information is transmitted together with the image data obtained by reading the radiographic image recorded on the recording sheet, from said at least one radiographic image reading apparatus to any one of said plurality of medical image processing apparatuses;

image processing means for processing the image data transmitted to said medical image processing apparatus; and counting means for counting a usage count number of each recording sheet on a basis of the recording sheet identification information received under control of said reception control means, weighting a count value in accordance with a set condition reflecting a degree of degradation in a characteristic of the recording sheet, and accumulating the weighted count value to store the accumulated count value into a storage section in correspondence with the recording sheet identification information.

11. The medical image processing apparatus according to claim 10, wherein said counting means weights the count value in accordance with at least one of a condition set for each radiographic image reading apparatus, a condition set for each installation environment of the radiographic image reading apparatus, and a condition set for each recording sheet.

12. The medical image processing apparatus according to claim 10, further comprising:

notification means for obtaining a comparison result by comparing the count value stored in said storing section with a set recommended usage count of the recording sheet, and notifying of a usage state of each recording sheet by image and/or voice on a basis of the obtained comparison result.

13. A recording sheet usage count evaluation apparatus for evaluating a usage count of each recording sheet and to be used with at least one radiation imaging apparatus for imaging an object by irradiating the object with radiation to record a radiographic image on the recording sheet, at least one radiographic image reading apparatus for reading the radiographic image recorded on the recording sheet to obtain image data, and a plurality of medical image processing apparatuses capable of processing the image data received from said at least one radiographic image reading apparatus, said apparatus comprising:

reception control means for controlling receiving operation to receive recording sheet identification information for use in identifying the recording sheet, when the recording sheet identification information is transmitted together with the image data obtained by reading the radiographic image recorded on the recording sheet, from said at least one radiographic image reading apparatus to any one of said plurality of medical image processing apparatuses; and counting means for counting a usage count number of each recording sheet on a basis of the recording sheet identification information received under control of said reception control means, weighting a count value in accordance with a set condition reflecting a degree of degradation in a characteristic of the recording sheet, and accumulating the weighted count value to store the accumulated count value into a storage section in correspondence with the recording sheet identification information.

14. The recording sheet usage count evaluation apparatus according to claim 13, wherein said counting means weights the count value in accordance with at least one of a condition set for each radiographic image reading apparatus, a condition set for each installation environment of the radiographic image reading apparatus, and a condition set for each recording sheet.

15. The recording sheet usage count evaluation apparatus according to claim 13, further comprising:

notification means for obtaining a comparison result by comparing the count value stored in said storage section with a set recommended usage count of the recording sheet, and notifying of a usage state of each recording sheet by image and/or voice on a basis of the obtained comparison result.

* * * * *